| United States Patent [19] | [11] Patent Number: 5,019,599 |
| Miki et al. | [45] Date of Patent: May 28, 1991 |

[54] DEODORIZING URETHANE FOAM AND PROCESS FOR ITS PRODUCTION

[75] Inventors: Yoshiaki Miki, Yokohama; Tsunehisa Ueda, Zushi, both of Japan

[73] Assignee: Nippon Zeon Co., Ltd., Tokyo, Japan

[21] Appl. No.: 326,982

[22] Filed: Mar. 22, 1989

[30] Foreign Application Priority Data

Mar. 25, 1988 [JP] Japan ................................ 63-71541

[51] Int. Cl.$^5$ ............................................ C08G 18/14
[52] U.S. Cl. ...................................... 521/99; 521/106; 521/119; 521/120; 521/123; 521/136; 524/112
[58] Field of Search ................ 521/99, 106, 119, 120, 521/123, 136; 524/112; 424/76.1, 76.2, 76.3, 76.9

[56] References Cited

U.S. PATENT DOCUMENTS

| 3,104,205 | 9/1963 | Hainer et al. | 424/76.9 |
| 3,412,111 | 11/1968 | Irwin et al. | 524/112 |
| 3,976,590 | 8/1976 | Yaz et al. | 252/182 |
| 4,339,550 | 7/1982 | Palinczar et al. | 424/76.3 |

FOREIGN PATENT DOCUMENTS

| 2034565 | 2/1987 | Japan | 424/76.2 |
| 2179464 | 8/1987 | Japan | 424/76.1 |

*Primary Examiner*—Maurice J. Welsh
*Attorney, Agent, or Firm*—Sherman and Shalloway

[57] ABSTRACT

A deodorizing urethane foam comprising a urethane foam substrate and a deodorizing component. The deodorizing component is composed of (A) a Diels-Alder reaction-type addition reaction product between an alpha,beta-unsaturated dicarboxylic anhydride and an olefin or a derivative of the reaction product and optionally (B) a copper compound. This urethane foam is produced by foaming a mixture of materials for the urethane foam substrate and the Diels-Alder reaction-type addition reaction product between an alpha,beta-unsaturated dicarboxylic anhydride and an olefin or its derivative of the reaction product and optionally the copper compound.

11 Claims, No Drawings

DEODORIZING URETHANE FOAM AND PROCESS FOR ITS PRODUCTION

This invention relates to a urethane foam having excellent deodorizing property.

Many conventional deodorants are in the form of a liquid or a powder. They may be directly used in spraying or sprinkling, but for other purposes, they are frequently used in combination with other materials, for example in a form impregnated in, or carried on, various substrates. A urethane foam is a suitable material for combination with a deodorant because it is easy to process and has a large surface area and particularly, an open-cellular urethane foam is air-permeable. For example, there have been proposed a sponge-like deodorant obtained by impregnating a liquid deodorant in an open-cellular foam (Japanese Laid-Open Patent Publication No. 116360/1985) and deodorizing filter obtained by impregnating an emulsion-type adhesive, a powdery activated carbon and a difficultly water-soluble solid acid in a urethane foam from which the cell membranes have been removed (Japanese Laid-Open Patent Publication No. 103518/1986). However, these deodorant materials have the defect that (1) the deodorants adhering to the surface of the foams are liable to exfoliate, (2) they have low water resistance and solvent resistance, and (3) the amount of the deodorant cannot be increased beyond a certain amount.

Japanese Laid-Open Patent Publication No. 145143/1985 describes that a deodorizing composition comprising an iron compound, ethyenediaminetetraacetic acid and alum is mixed together with a blowing agent during the production of a foamed resin such as a urethane or styrene foam. The method offers an improvement on the defect of the above impregnating method. It has been found however that since the deodorizing composition to be mixed obstructs foaming, the resulting foamed product gets out of shape, and the desired deodorizing property cannot be obtained. Moreover, as a basic problem, a deodorizing component having excellent properties which is to be included in such a urethane foam has not been known.

The present inventors, after conducting extensive investigations in order to solve the above problems, have now found that the use of a deodorizing component of a specific composition gives a deodorizing urethane foam having excellent deodorizing property and a good shape.

The present invention provides (1) a deodorizing urethane foam comprising a urethane foam substrate and a deodorizing component included therein, the deodorizing component being composed of a Diels-Alder reaction-type addition reaction product between an alpha,beta-unsaturated dicarboxylic anhydride and an olefin or a derivative of the addition reaction product [to be sometimes referred to as component (A)];

(2) a deodorizing urethane foam comprising a urethane foam substrate and a deodorizing component included therein, the deodorizing component being composed of (A) a Diels-Alder reaction-type addition reaction product between an alpha,beta-unsaturated dicarboxylic anhydride and an olefin or a derivative of the addition reaction product and (B) a copper compound; and (3) a process for producing a deodorizing urethane foam, which comprises foaming a mixture of materials for the urethane foam substrate with (I) a deodorizing component containing a Diels-Alder reaction-type addition reaction product between an alpha,-beta-unsaturated dicarboxylic anhydride and an olefin, or with (II) a deodorizing component containing (A) a Diels-Alder reaction-type addition reaction product between an alpha,beta-unsaturated dicarboxylic anhydride and an olefin and (B) a copper compound.

The Diels-Alder reaction-type addition reaction between the alpha,beta-unsaturated dicarboxylic anhydride and the olefin may be, for example, the Diels-Alder reaction between an alpha,beta-unsaturated dicarboxylic anhydride and a diolefin or the ene-reaction between an alpha,beta-unsaturated dicarboxylic anhydride and a monolefin [the ene-reaction is described in H. M. R. Hoffmann: Angew. Chem. Int. Ed., 8, 556 (1969)].

Specific examples of the alpha,beta-unsaturated dicarboxylic anhydride used in this invention are maleic anhydride, itaconic anhydride and citraconic anhydride. Of these, maleic anhyride is preferred from the viewpoint of reactivity and economy.

The diolefin which performs Diels-Alder reaction with the alpha,beta-unsaturated dicarboxylic anhydride is not particularly limited. Its specific examples include aliphatic conjugated diolefins such as butadiene, isoprene and piperylene; aliphatic trienes such as 1,3,5-hexatriene; cyclic conjugated polyunsaturated olefins such as cyclopentadiene, 1,3-cyclohexadiene and cyclooctatetraene; and aromatic compounds such as styrene, indene and naphthalene. Other diolefins may include the compounds described in M. C. Kloetzel et al., "Organic Reactions", vol. 4, pages 1–60 (John Wiley & Sons, Inc.). The monolefin which performs ene-reaction with the alpha,beta-unsaturated dicarboxylic anhydride is not particularly limited. Its specific examples include aliphatic monolefins such as propylene, isobutene, 1-butene, 2-butene, 1-pentene, 2-pentene, 2-methyl-1butene, 2-methyl-2-butene, 1-hexene, 2,2,4-trimethyl-1-pentene, 2,2,4-trimethyl-2-pentene, 1-decene, 1-octadecene and low-molecular-weight polymers obtained by polymerizing lower monolefins (e.g., ethylene or propylene) with Ziegler catalysts; cyclic monolefins such as cyclopentene, cyclohexene and cyclooctene; aliphatic or cyclic non-conjugated diolefins such as 1,4-pentadiene and 1,4-cyclohexadiene; higher unsaturated fatty acids such as oleic acid; and polymers having unsaturated bonds such as polybutadiene. Compounds resulting from substitution of an alkyl group, a phenyl group, etc. for at least hydrogen atom of these compounds may also be used.

The derivatives of the Diels-Alder reaction-type addition reaction product between the alpha,beta-unsaturated dicarboxylic anhydride and the olefin used in this invention is not limited in the method of its synthesis, and may have a structure derived by a known reaction from the Diels-Alder reaction-type addition reaction product between the alpha,beta-unsaturated dicarboxylic anhydride and the olefin. Specific examples are a hydrogenation reaction product of the Diels-Alder reaction-type addition reaction product between the alpha,beta-unsaturated dicarboxylic anhydride and the olefin, a compound obtained by converting the acid anhydride group of the above adduct into a carboxyl group and further performing the Diels-Alder reaction-type addition reaction with the olefin, and a compound obtained by hydrogenating this compound.

In the present invention, the Diels-Alder reaction-type addition reaction products between alpha,beta-unsaturated dicarboxylic anhydrides and olefins or their derivatives may be used singly or in combination with each other.

By using the above Diels-Alder reaction-type addition reaction product between the alpha,beta-unsaturated dicarboxylic anhydride and the olefin described above in combination with a copper compound as the deodorizing component, a urethane foam which can also have excellent mercaptan deodorizing ability can be obtained.

The copper compound [which may sometimes be referred to as the component (B)] used in this invention may be any of inorganic acid salts, organic acid salts, hydroxides, sulfides, complexes and oxides. Specific examples include copper sulfate, copper nitrate, cuprous chloride, cupric chloride, cuprous bromide, cupric bromide, cuprous iodide, copper carbonate, cupric hydroxide, cupric sulfide, copper cyanide, copper acetate, cupric citrate, copper gluconate, copper malate, copper glyoxylate, copper 2-ketoglutarate, copper pyruvate, copper oxaloacetate, acidic copper phosphate, copper pyrophosphate, copper chlorophyll, copper chlorophyllin sodium, copper chlorophyllin potassium, copper phthalocyanine, copper porphyrin, copper ethylenediaminetetraacetate, copper acetylacetonate, cuprous oxide, cupric oxide, copper oleate and copper naphthenate. Compounds containing copper in the form of, for example, a copper carboxylate in the polymer chain may also be used. The inorganic acid copper salts are preferred from the standpoint of price and availability, and the complexes, from the standpoint of safety.

When component (B) is used in this invention, the ratio of component (A) to component (B) can be properly selected according to the properties required of the desired product. Usually, the proportion of component (B) is 0.01 to 200 parts by weight, preferably 0.05 to 20 parts by weight, per 100 parts by weight of component (A). If the amount of component (B) is too small, the resulting deodorant may have the lowered ability to deodorize sulfur-type malodors. On the other hand, if it is too large, it may undesirably involve a toxicity problem. The copper compounds may be used singly or in combination with each other.

The deodorizing urethane foam of this invention can be obtained by incorporating the deodorant component comprising component (A) or both components (A) and (B) into the urethane foam substrate.

The deodorizing urethane foam of this invention may contain conventional deodorants, adsorbents (e.g., activated carbon or zeolite), fungicides, mold-proofing agents, coloring agents, pigments, antioxidants, ultraviolet absorbers and flame retardants in addition to the specific deodorant component described above so long as they do not impair the effects of the present invention.

The urethane foam substrate used in the present invention can be obtained basically by reacting and foaming main materials (i.e., an isocyanate compound and a compound having active hydrogen) for the urethane foam substrate in the presence of subsidiary materials such as a crosslinking agent, a catalyst, a blowing agent and a surface-active agent.

The isocyanate compound used as a main material for the urethane foam substrate is not particularly limited. Specific examples are diisocyanate compounds such as 4,4'-diphenylmethane diisocyanate, tolylene diisocyanate (TDI) and hexamethylene diisocyanate; and polyisocyanate compounds having unreacted isocyanate groups left at the terminals obtained by reacting these diisocyanate compounds with glycols, triols, etc. These isocyanate compounds may be used singly or in combination with each other.

The compound having active hydrogen to be used in combination with the isocyanate compound is neither limited in particular. Its specific examples include dihydric alcohols such as ethylene glycol, propylene glycol, 1,4-butanediol, 1,6-hexanediol, diethylene glycol and neopentyl glycol; trihydric or higher alcohols such as glycerol, trimethylolpropane, pentaerythritol, sorbitol, methylene glucoside and sucrose; polyhydric phenols such as pyrogallol and hydroquinone; aliphatic polycarboxylic acids such as succinic acid and adipic acid; aromatic polycarboxylic acids such as phthalic acid, terephthalic acid and trimellitic acid; ammonia; and primary amines such as ethylamine, propylamine and ethylenediamine. Other examples of the active hydrogen compound ar polyester polyols obtained by the reaction of the above alcohols with the above carboxylic acids; and polyether polyols obtained by the reaction of the above alcohols or phenols with ethylene oxide or propylene oxide.

The blowing agent for expanding the main materials for the urethane foam substrate may be, for example, water, or a halogenated aliphatic hydrocarbon such as methylene chloride or trichloromonofluoromethane.

Examples of the crosslinking agent include trihydric or higher, low-molecular-weight polyols such as glycerol, trimethylolpropane, triethanolamine and tetra-(hydroxypropyl)ethylenediamine.

Examples of the catalyst are tertiary amines such as N,N-dimethylethanolamine and ethylmorpholine; organotin compounds such as tin octenate and dibutyltin diacetate; organolead compounds such as lead octenate; and calcium carbonate. Other known catalysts may also be used.

The content of the deodorizing component in the deodorizing urethane foam of this invention is not particularly limited, and may be selected according to the purpose for which the deodorizing urethane foam is used. Usually, it is 0.05 to 20 % by weight based on the urethane foam substrate. If the amount of the decdorizing component is too small, the deodorizing ability of the resulting foam is insufficient. Generally, the deodorizing ability increases with increasing content of the deodorizing component. If, however, its content is too large, it may degrade the properties of the urethane foam.

In the present invention, the deodorizing component may be included into the urethane foam by a desired method. Usually, a urethane foam having excellent deodorizing ability and a good shape can be easily obtained by mixing materials for the urethane foam substrate (main materials and as required, subsidiary materials) with the deodorizing component, and foaming the resulting mixture. Preferably, in obtaining the mixture, all the deodorant component is mixed at a time with all the materials for the urethane foam substrate; or all the deodorizing component is mixed with part of the materials for the urethane foam substrate and the mixture is further mixed with the remaining materials for the urethane foam substrate.

Another method of incorporating the deodorizing component into the urethane foam substrate comprises producing the urethane foam substrate by a known method, and immersing it in a solution of the deodorizing component or coating the solution on the urethane foam substrate.

Thus, the present invention can give a deodorizing urethane foam having a higher deodorizing ability and a better shape than in the prior art.

The following Examples illustrate the present invention more specifically. All parts and percentages in the following Examples, Comparative Examples and Referential Examples are by weight unless otherwise specified.

REFERENTIAL EXAMPLE 1

DIALEN 610 (an alpha-olefin having 6 to 10 carbon atoms produced by Mitsubishi Chemical Co., Ltd.) and an equimolar proportion of maleic anhydride were introduced into an autoclave, and subjected to addition-reaction at 200° C. for 15 hours in the presence of a polymerization inhibitor. The unreacted alpha-olefin was removed under reduced pressure to give an ene-reaction product of the alpha-olefin and the maleic anhydride.

REFERENTIAL EXAMPLE 2

Maleic anhydride (68.6 parts) and 70 parts of toluene were introduced into a pressure autoclave, and melted at 55° C. Then, 0.162 part of hydroquinone was added, and 130.9 parts (corresponding to 1.1 moles of trans-1,3-pentadiene per mole of maleic anhydride) of crude trans-1,3-pentadiene composed of 40 % of trans-1,3-pentadiene, 20 % of cis-1,3-pentadiene and 40 % of pentanes was continuously added over 6 hours at 50° C. The temperature was then raised to 60° C., and the reaction was carried out for 3 hours. After the reaction, the reaction mixture was distilled at 90° C. under atmospheric pressure to remove volatile components to give 3-methyltetrahydrophthalic anhydride (melting point 61° C.) in a yield of 99 % as a Diels-Alder reaction product.

EXAMPLE 1

(Runs Nos. 1-1 to 1-5)

In each run, 100 parts of polyol (GR3000, a product of Sanyo Chemical Co., Ltd.) was mixed with each of the deodorizing components [component (A)] in each of the amounts indicated in Table 1. The mixture was mixed by a mixer with 42 parts of TDI-90 [a mixture of 2,4-TDI and 2,6-TDI (mixing ratio: 80:20); NCO index=105], 3.2 parts of water, 0.3 part of tin octenate, 0.2 part of triethylenediamine and 1.5 parts of silicone oil to allow them to react and foam and give a deodorizing urethane foam. The mixing recipe was set such that in the absence of the deodorizing component, the specific gravity of the urethane foam would be 0.03.

The foamed state of the resulting urethane foam was observed, and its specific gravity was measured.

One gram of the urethane foam was put in a 150 ml glass ampoule with a crown cap, and the ampoule was sealed up. The inside of the ampoule was purged with air containing 100 ppm of ammonia. After a predetermined period of time, the amount of ammonia in the ampoule was measured by gas chromatography, and the deodorizing rate was calculated.

The results are shown in Table 1.

COMPARATIVE EXAMPLE 1

(Runs Nos. 1-6 to 1-8)

Example 1 was repeated except that the deodorizing component was not used, or conventional deodorants were used instead of component (A) used in Example 1.

The results are also shown in Table 1.

TABLE 1

| Run No. | Deodorizing component Component (A) | Amount (parts) | Deodorizing urethane foam Specific gravity | Foamed condition | Ammonia deodorizing rate (%) (after 1 hour) |
|---|---|---|---|---|---|
| Invention | | | | | |
| 1-1 | the ene-reaction product of Referential Example 1 | 1 | 0.030 | good | 100 |
| 1-2 | 3-methyltetrahydrophthalic anhydride of Referential Example 2 | 1 | 0.030 | good | 100 |
| 1-3 | dodecenylsuccinic anhydride (*1) | 1 | 0.030 | good | 100 |
| 1-4 | " | 0.5 | 0.030 | good | 99 |
| 1-5 | " | 3 | 0.030 | good | 100 |
| Comparison | | | | | |
| 1-6 | citric acid | 1 | 0.036 | slightly turned brown | 43 |
| 1-7 | ferrous sulfate/ascorbic acid (*2) | 1 | — | expansion ratio low, uncured, turned brown | measurement impossible |
| 1-8 | not added | 0 | 0.030 | good | 22 |

(*1): Tradename DSA (a product of Sanyo Chemical Co., Ltd.)
(*2): Ascorbic acid was added in an amount of 1% by weight based on ferrous sulfate.

The results given in Table 1 show that the urethane foams provided by this invention had a good foamed condition and excellent deodorizing ability.

EXAMPLE 2

(Runs Nos. 2-1 to 2-5)

Example 1 was repeated except that 100 parts of component (A) shown in Table 2 and component (B) in the amounts indicated were used as the deodorizing component. Observation of the foamed state, measurement of specific gravity, an ammonia deodorizing test, a methylmercaptan deodorizing test (methylmercaptan 150 ppm) and a hydrogen sulfide deodorizing test (hydrogen sulfide 100 ppm) were performed on the resulting urethane foams as in Example 1.

The results are shown in Table 2.

COMPARATIVE EXAMPLE 2

(Runs Nos. 2-6 to 2-8)

The same tests as in Example 2 were conducted on the urethane foams obtained in Comparative Example 1.

The results are shown in Table 2.

The results given in Table 2 show that the deodorizing urethane foams containing components (A) and (B) as the deodorizing component had a good foamed condition and good deodorizing ability.

product, and (B) from 0.05 to 20 parts by weight, per 100 parts by weight of component (A) of a copper compound selected from the group consisting of inorganic acid salts, monomeric organic acid salts, hydroxides, sulfoxides, complexes, and oxides.

TABLE 2

| | | Deodorizing component | | |
|---|---|---|---|---|
| | | | Component (B) | Amount |
| Run No. | Component (A) | Type | Amount (parts) | added (%) |
| Invention | | | | |
| 2-1 | the ene-reaction product of Referential Example 1 | copper sulfate pentahydrate | 2 | 1 |
| 2-2 | 3-methyltetrahydrophthalic anhydride of Referential Example 2 | copper chlorophyll | 2 | 1 |
| 2-3 | dodecenylsuccinic anhydride (*1) | copper oleate | 7.5 | 0.5 |
| 2-4 | " | copper oleate | 7.5 | 1 |
| 2-5 | " | copper naphthenate | 5 | 1 |
| Comparison | | | | |
| 2-6 | citric acid | — | — | 1 |
| 2-7 | ferrous sulfate/ascorbic acid (*2) | — | — | 1 |
| 2-8 | not added | — | — | 0 |

| | Deodorizing urethane foam | | | |
|---|---|---|---|---|
| | | | Deodorizing rate (%) | |
| Run No. | Specific gravity | Foamed condition | Ammonia (after 1 hour) | Methylmercaptan (after 24 hours) | Hydrogen sulfide (after 24 hours) |
| Invention | | | | | |
| 2-1 | 0.030 | good | 100 | 98 | 99 |
| 2-2 | 0.030 | good | 100 | 80 | 72 |
| 2-3 | 0.030 | good | 100 | 95 | 93 |
| 2-4 | 0.030 | good | 100 | 100 | 99 |
| 2-5 | 0.030 | good | 100 | 99 | 95 |
| Comparison | | | | | |
| 2-6 | 0.036 | slightly turned brown | 45 | 41 | 17 |
| 2-7 | — | expansion ratio low, uncured, turned brown | measurement impossible | | |
| 2-8 | 0.030 | good | 22 | 39 | 21 |

(*1) and (*2) are the same as the footnotes to Table 1.

We claim:

1. A deodorizing urethane foam comprising a urethane foam substrate and from 0.05 to 20% by weight, based on the urethane foam substrate, of a deodorizing component included therein, the deodorizing component comprising a Diels-Alder reaction-type addition reaction product selected from the group consisting of (1) a Diels-Alder reaction product between an alpha, beta-unsaturated dicarboxylic anhydride and a diolefin and (2) an ene-reaction product between an alpha, beta-unsaturated dicarboxylic anhydride and a monoolefin, or a derivative of the addition reaction product.

2. The deodorizing urethane foam of claim 1 in which the Diels-Alder reaction-type addition reaction product is said Diels-Alder reaction product between an alpha, beta-unsaturated dicarboxylic anhydride and a diolefin.

3. The deodorizing urethane foam of claim 1 wherein the Diels-Alder reaction-type addition reaction product is the ene-reaction product.

4. A deodorizing urethane foam comprising a urethane foam substrate and 0.05 to 20% by weight based on the weight of the urethane foam, of a deodorizing component included therein, the deodorizing component comprising (A) a Diels-Alder reaction-type addition reaction product selected from the group consisting of (1) a Diels-Alder reaction product between an alpha, beta-unsaturated dicarboxylic anhydride and a diolefin and (2) an ene-reaction product between an alpha, beta-unsaturated dicarboxylic anhydride and a monoolefin, or a derivative of the addition reaction 5. A deodorizing urethane foam according to claim 4 wherein the copper compound (B) is selected from the group consisting of copper sulfate, copper nitrate, cuprous chloride, cupric chloride, cuprous bromide, cypric bromide, cuprous iodide, copper carbonate, cupric hydroxide, cupric sulfide, copper cyanide, copper acetate, cupric citrate, copper gluconate, copper malate, copper glyoxylate, copper 2-ketoglutarate, copper pyruvate, copper oxaloacetate, acidic copper phosphate, copper pyrophosphate, copper chlorophyll, copper chlorophyllin sodium, copper chlorophyllin potassium, copper phthalocyanine, copper prophyrin, copper ethylenediamine-tetraacetate, copper acetylacetonate, cuprous oxide, cupric oxide, copper oleate and copper naphthenate.

6. The deodorizing urethane foam of claim 1 or claim 4 wherein the amount of the deodorizing component is from 0.5 to 1% by weight, based on the weight of the urethane foam.

7. A process for producing a deodorizing urethane foam, which comprises foaming a mixture of materials for the urethane foam substrate with (I) a deodorizing component containing a Diels-Alder reaction-type addition reaction product selected from the group consisting of (1) a Diels-Alder reaction product between an alpha, beta-unsaturated dicarboxylic acid and a diolefin and (2) an ene-reaction product between an alpha, beta-unsaturated dicarboxylic acid and a monoolefin, or a derivative of the addition reaction product, or with (II)

a deodorizing component containing (A) a Diels-Alder reaction-type addition reaction product selected from the group consisting of (1) a Diels-Alder reaction product between an alpha, beta-unsaturated dicarboxylic anhydride and a diolefin and (2) an ene-reaction product between an alpha, beta-unsaturated dicarboxylic anhydride and a monoolefin, or a derivative of the addition reaction product, and (B) a copper compound selected from the group consisting of inorganic acid salts, monomeric organic acid salts, hydroxides, sulfides, complexes and oxides.

8. The process of claim 7 wherein the deodorizing component (I) or (II) is present in an amount of from 0.05 to 20% by weight, based on the weight of the urethane foam substrate.

9. The deodorizing urethane foam of claim 1 wherein said derivative of the addition reaction product is selected from the group consisting of hydrogenation products of the Diels-Alder reaction-type addition product, compounds obtained by converting the acid anhydride group of the addition reaction product to an acid and further reaching with an olefin, and the hydrogen-action products of said compounds.

10. The deodorizing urethane foam of claim 4 wherein said derivative of the addition reaction product is selected from the group consisting of hydrogenation products of the Diels-Alder reaction-type addition product, compounds obtained by converting the acid anhydride group of the addition reaction product to an acid and further reaching an olefin, and the hydrogen-action products of said compounds.

11. The process of claim 7 wherein said derivative of the addition reaction product is selected from the group consisting of hydrogenation products of the Diels-Alder reaction-type addition product, compounds obtained by converting the acid anhydride group of the addition reaction product to an acid and further reaching an olefin, and the hydrogen-action products of said compounds.

* * * * *